United States Patent [19]

Ballard et al.

[11] Patent Number: 4,524,198

[45] Date of Patent: Jun. 18, 1985

[54] POLY(1,2-DISUBSTITUTED CYCLOHEXA-3,5-DIENES

[75] Inventors: Denis G. H. Ballard, Littleton; Andrew Courtis, Hightown; Ian M. Shirley, Barnton, all of England

[73] Assignee: Imperial Chemical Industries Limited, London, England

[21] Appl. No.: 585,373

[22] Filed: Mar. 2, 1984

Related U.S. Application Data

[62] Division of Ser. No. 433,097, Oct. 6, 1982, Pat. No. 4,476,296.

[30] Foreign Application Priority Data

Oct. 6, 1981 [GB] United Kingdom ............... 8130114
Oct. 6, 1981 [GB] United Kingdom ............... 8130115
Oct. 6, 1981 [GB] United Kingdom ............... 8130116

[51] Int. Cl.³ ............................................. C08F 32/06
[52] U.S. Cl. .................................... 526/292.1; 424/78; 435/253; 526/292.3; 526/292.4; 526/292.5; 526/292.6; 526/309
[58] Field of Search ............... 526/292.1, 292.3, 292.4, 526/292.5, 292.6, 309, 292.9

[56] References Cited

U.S. PATENT DOCUMENTS 3,431,221 3/1969 Hoess.

FOREIGN PATENT DOCUMENTS 6402650 3/1964 Netherlands.
1128896 10/1968 United Kingdom.

OTHER PUBLICATIONS

Vankerckhoven et al., Macromolecules, 1972, 5, 541–546.
Hayama et al., Kogyo Kagaku Zasshi, 1969, 72, 608–609, 1589–1593, 2334–2336.
Niino, Kogyo Kagaku Zasshi, 1971, 74, 499–502, 1042–1004.
Naumova, and Tsykalo, Vyoskomol. Soed., 1961, 3, 1031.
Erogeev, Sb. Nauch. Rabot. Akad. Nauk. Belonissk SSR, 1961, 9, 71.
Imanishi et al., Journal of Macromolecular Science, Chemistry A3, 1969, 223.
Marval et al., Journal of the American Chemical Society, 1959, 81, 448–452.
Rinehart, J.P.S. C, 1969, 7.
Dolgoplosk et al., European Polymer Journal, 1973, 9, 895.
Marvel and Hartzell, Journal of the American Chemical Society, 1964, 2, 3277–3295.
LeFebve and Dawans, Journal of Polymer Science, 1965, 3, 1553.
Cassidy, Marven and Ray, Journal of Polymer Science, 1965, 3, 1553.
Frey, Hasegawa and Marvel, Journal of Polymer Science, 1963, 1, 2057.
Durham et al., Journal of Polymer Science, Polymer Chemistry Edition, 1978, 16, 1147–1157.
Stoessel et al., Clay Minerals, 1977, 12, 255–259.
Jones, et al., Journal of Polymer Science, Polymer Chemistry Edition, 1981, 19, 89–101.
Yamomoto et al., Bull. Chem. Soc., Japan, 1978, 51, 2091–2097.
Ibuki et al., Chem. Pharm. Bull., 1982, 30, pp. 802 and 2369.

*Primary Examiner*—Christopher A. Henderson
*Attorney, Agent, or Firm*—Cushman, Darby & Cushman

[57] ABSTRACT

A process for the preparation of polymeric compositions which comprise novel polymers and copolymers of certain 1,2-disubstituted-cyclohexadienes, aromatization of such polymers in the form of inter alia fibres, and novel aromatic polymers.

5 Claims, No Drawings

POLY(1,2-DISUBSTITUTED CYCLOHEXA-3,5-DIENES)

CROSS REFERENCE TO RELATED APPLICATIONS

This application is a division of our earlier copending application Ser. No. 433,097 filed Oct. 6, 1982, now U.S. Pat. No. 4,476,296.

The invention relates to ring-containing polymers, to processes for the production thereof and to polymeric blends comprising such polymers.

Homopolymers of 1,4-cyclohexadiene and copolymers thereof with sulphur dioxide are known. Whilst we have been unable to polymerise 1,2-dihydroxycyclohexa-3,5-diene by free radical or ionic polymerisation we have now found that certain derivatives of 1,2-disubstitutedcyclohexa-3,5-diene and certain homologues and analogues thereof can, under suitable conditions, be homopolymerised, or copolymerised with suitable polymerisable comonomers to produce polymers which have a useful combination of properties.

Known polymers which have aromatic rings in the backbone thereof are, because of their intractible nature, often difficult to form or shape; and where such polymers are polyphenylenes they often contain halogen impurities which are due to their mode of preparation.

We have found that certain of the aforementioned poly(1,2-disubstitutedcyclohexa-3,5-dienes) can be readily shaped or formed and then converted into polyphenylenes and that such polyphenylenes often contain no or less halogen impurities than polyphenylenes known hitherto.

Accordingly, a first aspect of the present invention provides a process for the preparation of polymeric compositions which process comprises treating a polymerisable composition which comprises a 1,2-disubstituted-cyclohexa-3,5-diene or homologue or analogue thereof under polymerisation conditions for the polymerisable composition, which 1,2-substituents, which may be the same or different, are not hydroxy groups and do not unduly inhibit the polymerisation of the polymerisable composition.

A second aspect of the present invention provides polymeric compositions comprising a polymer which is preparable by a process at least one step of which comprises treating a polymerisable composition which comprises a 1,2-disubstituted-cyclohexa-3,5-diene or homologue or analogue thereof under polymerisation conditions for the polymerisable composition.

A third aspect of the present invention provides a process for the preparation of a polymer having aromatic rings in the backbone thereof which process comprises treating a polymer which has 1,2-disubstituted cyclohexenylene rings in the polymer backbone under conditions such that the 1,2-substituents are eliminated from at least substantially all of the said cyclohexenylene rings.

A fourth aspect of the present invention provides polymeric compositions comprising a polymer having a structure which may be represented by the general formula:

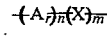   I wherein the residues Ar and X, where X is present, may vary from unit to unit in the polymer chain, Ar represents a divalent aromatic or substituted aromatic group and X, is a residue of one or more polymerisable comonomers as hereinafter defined and n, and m have the meanings hereinafter ascribed to them, with the proviso that where Ar represents a p-phenylene group and m is zero n is greater than 120 and preferably the polymer has a crystallinity of at least 40%, more preferably at least 60% and where Ar represents a paraphenylene group and X is —SO—$_2$— the polymeric composition has a number average molecular weight of more than 5,000.

By "polymerisable comonomer" we mean a compound which can be reacted under polymerisation conditions with a 1,2-disubstituted-cyclohexa-3,5-diene which has 1,2-substituents as hereinbefore defined to form a copolymer therewith.

Examples of suitable polymerisable comonomers which may be used in the present invention include vinyl monomers, for example, olefinic hydrocarbons, e.g. styrene and ethylene, methacrylates, vinyl halides, vinyl esters, acrylonitrile and tetrafluoroethylene; and compounds such as carbon monoxide, carbon dioxide and sulphur dioxide.

Preferably a polymerisable comonomer, where it is used in the present invention, generates a "stable" radical, by which we mean a propagating radical that is stabilised by an electron withdrawing group, e.g. phenyl, cyano, acyl, since we have found that polymerisable compositions which comprise, in addition to the 1,2-disubstituted-cyclohexa-3,5-diene, such polymerisable comonomers give polymeric compositions of higher molecular weight than polymerisable compositions comprising polymerisable comonomers which generate active radicals. As examples of polymerisable comonomers which generate stable radicals we would mention inter alia methyl methacrylate, styrene and acrylonitrile.

Preferably the 1,2-substituents in the 1,2-disubstituted-cyclohexa-3,5-diene or homologue or analogue thereof of which the polymerisable composition which is used in the process of the first aspect of the present invention is comprised are cis to each other since such compounds may be derived from cis-1,2-dihydroxycyclohexa-3,5-dienes which may be readily prepared by biochemical processes as is more fully described in our United Kingdom patent application No. 8130116. However, we do not exclude the possibility that the aforesaid substituents may be trans to each other.

As examples of the aforesaid 1,2-substituents we would mention inter alia acyloxy, carbonate, alkoxy, amide, halide, thioester, urethane and xanthate substituents.

Preferably the 1,2-disubstituted-cyclohexa-3,5-diene of which the polymerisable composition which is used in the first aspect of the present invention is comprised has a structure which may be represented by the general formula:

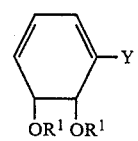   II wherein each $R^1$, which may be the same or different, is acyl, e.g. aroyl or alkanoyl, or $R^2OCO-$, where $R^2$ is aryl or an alkyl group having up to ten carbon atoms;

and Y is hydrogen, halogen, or an alkyl group having up to four carbon atoms.

Preferably the polymer of which the polymeric composition according to the second aspect of the present invention is comprised has a structure which may be represented by the general formula:

$$\left(\underset{\underset{OR^3}{\phantom{X}}\underset{OR^3}{\phantom{X}}}{\boxed{\phantom{XXX}}}^{Y}\right)_n (X)_{\overline{m}} \qquad \text{III}$$

wherein the cyclohexenylene ring and the residue X, where X is present, may vary from unit to unit along polymer chain; each $R^3$, which may be the same or different, is hydrogen or $R^1$, where $R^1$ has the meaning hereinbefore ascribed to it; X, and Y have the meanings hereinbefore ascribed to them; n and m are whole numbers; and the ratio of n:m lies in the range 1:0 to 1:100.

Preferably the polymer of which the polymeric composition which is used in the third aspect of the present invention is comprised has a structure which may be represented by the general formula:

$$\left(\underset{\underset{OR^3}{\phantom{X}}\underset{OR^3}{\phantom{X}}}{\boxed{\phantom{XXX}}}\right)_n (X)_{\overline{m}} \qquad \text{IV}$$

wherein the cyclohexenylene ring and the residue X, where X is present, may vary from unit to unit along the polymer chain; each $R^3$, which may be the same or different, X, n and m have the meanings hereinbefore ascribed to them. $R^1$, in general formula II and $R^3$, in general formulae III and IV, are preferably (a) aroyl groups, (b) alkanoyl groups having up to eight carbon atoms and lacking a hydrogen atom on the carbon atom adjacent the carboxy group or (c) $R^2OCO-$ in which $R^2$ has the meaning hereinbefore ascribed to it; and more preferably are $CH_3OCO-$ groups.

In general formulae II and III, Y is preferably hydrogen, chlorine, methyl or ethyl, and more preferably is hydrogen because in the polymer in which Y is hydrogen at least a portion of the cyclic rings may be readily aromatised.

In polymers of general formulae III and IV, in substantially all of the cyclic rings, each of the bonds which bind the cyclic ring into the polymer backbone is preferably attached to a carbon atom adjacent the olefinic double bond in the cyclic ring, i.e. the cyclic rings are bonded in the polymer backbone at the 3,6-positions.

In polymers of general formula I Ar is preferably a phenylene ring and more preferably the linkages by which the phenylene rings are bonded in the polymer backbone are para to each other.

In polymers of general formulae I, III, and IV, n is preferably greater than about 400; m is preferably 0 or the ratio of n:m, where group X is present, is in the range 50:1 to 1:50; the cyclic rings and the group X, where present, preferably form an alternating copolymer; and the group X, where present, is preferably the residue of a polymerisable comonomer chosen from the group consisting of $$-CH_2CHAr-, \ -CH_2\underset{\underset{CO_2R^4}{|}}{\overset{\overset{CH_3}{|}}{C}}-, \ -CHR^2CH_2-, \ -CH_2-\underset{\underset{O_2CR^4}{|}}{CH}-,$$

$$-CH_2-\underset{\underset{CN}{|}}{CZ}-, \ -CH_2CHCl-, \ -CF_2CF_2-, \ -CO-,$$

$$\text{and } -SO_2-,$$

(where Z is a halogen atom or $R^4$ and $R^4$ is hydrogen or $R^2$, where $R^2$ has the meaning hereinbefore ascribed to it) and more preferably X is $-CH_2CHPh-$, $-CH_2CMeCO_2Me-$, or $-CH_2CHCN-$.

Certain of the 1,2-disubstituted-cyclohexadienes for use in the process of the first aspect of the present invention may often be obtained via a biological pathway. For example, cis-1,2-dihydroxycyclohexa-3,5-dienes may be prepared by suitable micro-organisms, e.g. a mutant strain of Pseudomonas putida, and the hydroxy groups thereof can be converted into suitable derivatives, e.g. ester and carbonate derivatives, by techniques well known in the art. For example, the ester derivatives can be prepared by reacting the aforesaid dihydroxy compounds with acyl halides or acyl anhydrides. For ease of polymerisation, the ester or carbonate derivatives are preferably used in the first aspect of the present invention.

The aforesaid mutant strain of Pseudomonas putida may be prepared by treating a naturally occurring Pseudomonas putida assigned the numerical designation NCIB 11680, which can use toluene and benzene as sole sources of carbon for growth, under mutuating conditions therefore to give a mutant strain which is no longer capable of utilizing toluene or benzene as a sole source of carbon for growth and which, when grown on a pyruvate medium in the presence of toluene, excretes a substance which has a UV absorbance peak at about 265 nanometers.

Preferably the aforesaid mutation is effected by treatment with a suitable mutagen, for example, by treatment with N-methyl-N'-nitro-N-nitrosoguanidine, which treatment can conveniently be effected by a process described by Ornston, Journal of Biological Chemistry, 1966, Volume 241, pages 3800–3810.

The naturally occurring specific species of Pseudomonas putida from which the aforementioned mutant strain can be prepared has been deposited with the National Collection of Industrial Bacteria, Torrey Research Station, P. O. Box 31, 135 Abbey Road, Aberdeen, where it has been assigned the numerical designation NCIB 11680.

The cells of the aforementioned mutant strain may be grown in conventional growth media as a continuous process, e.g. in a chemostat, however, a batch process is preferred, particularly preferably a fed batch process and more particularly preferably a fed batch process in which the cells are induced for aromatic oxidation by exposure to an aromatic compound, preferably toluene, for a period of at least 1 hour. The mutant organism of Pseudomonas putida is grown in a growth medium which comprises an aqueous mineral salts solution and a carbon source. The aqueous mineral salts solution supplies the following major and minor elements: nitrogen (e.g. as $NH_4^+$); phosphorus (e.g. as $PO_4^{3-}$); potassium (as $K^+$); magnesium (as $Mg^{2+}$); sodium (as $Na^+$); chlorine (as $Cl^-$;) iron (as $Fe^{2+}$ or $Fe^{3+}$); sulphur (e.g.

as $SO_4^{2-}$); copper (as $Ca^{2+}$); it typically has the composition:

|  | g/liter |
|---|---|
| concentrated $H_3PO_4$ | 0.7 |
| $MgSO_4.7H_2O$ | 1.6 |
| $K_2HPO_4.3H_2O$ | 0.9 |
| $(NH_4)_2SO_4$ | 1.5 |
| $FeSO_4$ | 0.025 |
| $CuSO_4.5H_2O$ | 0.001 |
| $MnSO_4.4H_2O$ | 0.005 |
| $ZnSO_4.7H_2O$ | 0.005 |
| $CaCO_3$ | 0.065 | and is adjusted to pH 7.0 before use with liquid ammonia, or with sodium hydroxide. The suitable carbon source may be, for example, pyruvic acid, acetic acid, glucose or ethanol. The concentration of carbon source can vary over a wide range but is generally between 1% (w/v) and 5% (w/v). Oxygen or an oxygen containing gas must be present during the growth period. The temperature of the medium during the growth period can vary considerably but normally will be in the range of 30° C. to 35° C. The pH of the medium is kept within the range 5.5 to 8.0 during growth and preferably at 7.0 to 7.5.

Although the size of culture can vary considerably, (for instance between 5 and 1000 liters), typically the mutant organism is inoculated into 40 liters of a suitable medium in a stirred fermenter to give an initial cell density of approximately 0.2 grams cell dry weight per liter of medium. After 7 to 12 hours growth when the cell density is approximately 1 to 5 grams cell dry weight per liter, fresh medium is added to the culture for the duration of the experiment at a rate of typically 1 to 2.5 liters per hour (for a 40 liter culture). After a further 1 to 6 hours, a monocyclic aromatic hydrocarbon, e.g. toluene, is added to the culture as a vapour in the air-stream, or directly as a liquid, at a rate of 5 to 20 grams per hour.

When the culture has been induced for aromatic oxidation, normally after 1 to 15 hours induction the cells are harvested by centrifugation.

The harvested cells are resuspended in a dilute aqueous mineral salts solution which is deficient in or lacks a source of at least one essential element required for cell growth such that little and preferably no cell growth occurs. Preferably the aforesaid at least one essential element is nitrogen. Typically, for the essential elements which are present in the dilute aqueous mineral salts solution which is deficient in or lacks a source of at least one essential element, the concentration and the form in which such elements are present are as hereinbefore described with regard to the typical composition of a growth medium. Typically the concentration of resuspended cells is 10 to 50 grams dry weight per liter. The resuspended cells are kept at a temperature of 30° C. to 35° C. and the pH maintained between 7.5 and 8.5. Oxygen or an oxygen containing gas is added to the cell suspension such that the oxygen tension is kept at greater than 1% of saturation. A metabolisable carbon substrate is fed, preferably as a continuous feed, to the cell suspension such that the concentration of the metabolisable carbon substrate is maintained at a suitable concentration, preferably between 0.1% (w/v) and 0.5% (w/v). Examples of suitable metabolisable carbon substrates include inter alia, alcohols, acetic acid, pyruvic acid and glucose. Preferably the metabolisable carbon substrate is an alcohol having 1 to 4 carbon atoms, more preferably ethanol.

The aromatic hydrocarbon, e.g. benzene, chloro-benzene, toluene, may be added to the cell suspension as a vapour in the air-stream but preferably is added directly mixed with the alcohol.

Where a mixture of aromatic hydrocarbon and alcohol is added the ratio of aromatic hydrocarbon to alcohol is typically in the range 1:2 to 4:1 by weight.

The rate of addition of the aromatic hydrocarbon is typically about 10 grams per liter of cell suspension per hour though this value may vary widely. The productive lifetime of the cell suspension is normally between 10 and 30 hours.

After this period of time the cells are removed by centrifugation and may be again resuspended in fresh medium and the process repeated. The supernatant liquor typically contains 5 to 30 grams per liter of a cis-1,2-dihydroxy, 1-2,-dihydrocyclohexa-3,5-diene or a homologue or analogue thereof.

The cyclic dihydroxy products for use in the process of the present invention are preferably extracted from the aqueous reaction mixture by solvent extraction with a suitable polar solvent. Examples of polar solvents which may be used include inter alia ethyl acetate, diethyl ether and methylene chloride. More preferably continuous extraction procedures are employed.

Whilst the 1,2-disubstituted-cyclohexadiene derivatives which are used in the process of the first aspect of the present invention are conveniently obtained via a biochemical pathway we do not exclude the possibility that they may be obtained by conventional organic synthesis or that the 1,2-substituents may be trans. For example, U.S. Pat. No. 3,755,080 describes the microbial conversion of naphthalenes to 1,2-dihydro-1,2-trans-di-hydroxy derivatives thereof using a Nocardia species of bacteria; Nakajima, et.al. describe the chemical synthesis of cis- and trans-1,2-dihydroxycyclohexane-3,5-diene in Chemische Berichte, 1959, Volume 92, pages 163–172 and 1956, Volume 89, pages 2224–9 respectively; and Platt et al describe the chemical synthesis of trans-1,2-diacetoxycyclohexa-3,5-diene in Synthesis, 1977, Volume 7, pages 449–50.

The polymerisation process of the first aspect of the present invention may be initiated by conventional olefin polymerisation catalysts and free radical initiation is preferred.

The polymerisation process of the first aspect of the present invention may be effected on a neat polymerisable composition; on a solution of the polymerisable composition in a suitable organic solvent, for example a hydrocarbon, e.g. toluene and benzene, a halohydrocarbon, e.g. 1,1,2-trichloro-1,2,2-trifluoroethane, a ketone, e.g. acetone and methyl ethyl ketone, or an ester, e.g. ethyl acetate; or on a suspension, dispersion or emulsion of the polymerisable composition which may be in an aqueous media, e.g. water, or in a suitable organic liquid, e.g. perfluoromethyldecalin, benzene or tetrafluoroethylene tetramer. Preferably the polymerisation is carried out on neat 1,2-disubstituted-cyclohexa-3,5-diene or a homologue or analogue thereof or in the presence of a suitable organic liquid.

The temperature at which the process of the first aspect of the present invention is carried out depends inter alia on the thermal stability of the 1,2-disubstituted-cyclohexa-3,5-diene and typically is carried out in the range 10° C. to 100° C.

The polymerisable composition used in the process of the first aspect of the present invention may comprise one or more of the aforesaid cyclohexadiene derivatives or a mixture of one or more of the aforesaid cyclohexadiene derivatives and one or more polymerisable comonomers. Where one or more polymerisable comonomers is/are present it/they may provide up to 99 mole % of the polymeric product. For example, where the polymerisable comonomer is styrene we have prepared copolymers which have a styrene content which varies from 1 to 99 mole %.

The polymeric compositions prepared by the process of the first aspect of the present invention typically have molecular weights of at least tens of thousands and often of hundreds of thousands.

The polymeric compositions of the second aspect of the present invention arre readily soluble in organic solvents, for example ketones, e.g. acetone; esters, e.g. ethyl acetate; hydrocarbons, e.g. toluene; halogenated hydrocarbons, e.g. chloroform; polar aprotic solvents, e.g., dimethyl formamide, and dimethyl sulphoxide; and protic solvents, e.g. trifluoroacetic acid and acetic acid. Films and fibres can be readily prepared from such solutions.

The polymeric compositions of the second aspect of the present invention may be fabricated by conventional techniques to produce products, e.g. fibres and films.

The polymeric compositions of the second aspect of the present invention readily form polymeric blends with suitable polymers. For example, a polymeric composition of the second aspect of the present invention may be readily mixed with, e.g. dissolved in, a suitable monomer which is then polymerised. Alternatively, the aforesaid polymeric composition and a suitable polymer may be dissolved in a common solvent and a polymeric blend recovered therefrom. As examples of suitable polymers of which the blend may be comprised we would mention inter alia polystyrene, polyphenylene oxide, and polyethylene terephthalate.

Where, in polymers of general formula III the groups $R^3$ represent hydrogen, such polymeric compositions can be prepared by hydrolisis of, for example, the corresponding ester. Techniques for effecting such hydrolisis are well known in the art.

Although we do not exclude the possibility that the process of the third aspect of the present invention may be carried out by treating the polymeric composition comprising a polymer of general formula IV in solution in a suitable solvent, e.g. squalane or sulpholane, it is often preferred that a neat polymeric composition comprising a polymer of general formula IV is employed.

Whilst the process of the third aspect of the present invention may be carried out by treating the polymeric composition of general formula IV with a suitable reagent, often subjecting the aforesaid polymeric composition to a suitable heat treatment is sufficient to effect aromatisation. Suitable heat treatments typically comprise heating the aforesaid polymeric composition for several hours at a temperature of, for example, 100° C. to 300° C. It will be appreciated that the exact conditions used will depend on the particular polymeric composition which is used and on the substituent groups which are being eliminated. For example, where acetate groups are being eliminated a temperature in the range 260° C. to 290° C. is often convenient; where benzoate groups are being eliminated a temperature in the range 280° C. to 320° C. is often convenient; where methyl carbonate groups are being eliminated a temperature about 250° C. is often convenient. It is preferred that carbonate groups are eliminated since such elimination can be effected at lower temperatures. Where carbonate groups are eliminated elimination is preferably effected in the presence of a suitable reagent. As examples of suitable reagents we would mention metal salts, e.g. halides of alkaline earth metals, e.g. potassium bromide, and bases of alkaline earth metals, e.g. potassium methoxide and potassium hydroxide.

It is often preferred that the process of the third aspect of the present invention is carried out on a polymeric composition which is in the form, e.g. of a film or fibre, which it is desired that the product of the process adopt. Furthermore, it is often preferred that the shaped and/or formed cyclohexenylene polymer is subjected to a tensile stress during treatment under the aforesaid conditions since such a stress tends to increase the tensile modulus of the resulting product, e.g. a fibre.

Where the process of the third aspect of the present invention is carried out on a polymer which is in fibrous form, the fibres are conveniently prepared by dry spinning the polymer from a suitable solvent, e.g. methylene chloride. The fibres may then be subjected to a suitable heat treatment. For example, the heat treatment may be effected in vacuo; or in an inert atmosphere, e.g. nitrogen.

The resulting polymer is often at least 90% polyphenylene as indicated by microanalysis and IR spectroscopic analysis.

Accordingly, a fifth aspect of the present invention provides a process for the production of a fibre which is substantially polyphenylene which process comprises subjecting a fibre of a suitable cyclohexenylene polymer to a suitable heat treatment in an appropriate atmosphere, preferably whilst the fibre is under a tensile stress to orientate the molecules thereof.

We do not exclude the possibility that the process of the third aspect of the present invention may be carried out on a polymer which has substantially a three dimensional shape, e.g. a solid cube. Where elimination is effected on a polymer of such a shape and where the polymer comprises suitably volatile substituents, or derivatives thereof, which are eliminated during the process, a foamed product may be produced. Where it is desired to produce a foamed product it is often preferred that the elimination reaction is effected by induction heating.

The polymeric compositions of the fourth aspect of the present invention typically have molecular weights of at least tens of thousands and often have decomposition temperatures of more than 250° C. although it will be appreciated that the decomposition temperature will depend on the nature and amount of the polymerisable comonomer where present.

It will be appreciated that as the ratio of n:m in general formula I increases, the modulus of the resulting polymer increases to give a polymer of very high modulus, particularly when the polymer chains are orientated.

The polymeric compositions of the fourth aspect of the present invention readily form polymeric blends with suitable polymers, in which polymeric blends the polymers are often molecularly dispersed. As examples of such suitable polymers we would mention inter alia polyethylene terephthalate, polymethyl methacrylate, nylon, polyethersulphone, polycarbonate, polystyrene, and polyphenylene oxide.

The quantity of the polymeric composition of the fourth aspect of the present invention which is used in the aforementioned polymeric blends depends inter alia on the properties required in the blend and on the particular polymeric composition which is used. The weight ratio of the polymeric composition to the suitable polymer may be between 1:2 and 1:1000 and preferably is between 1:4 and 1:20.

A polymeric blend comprising a polymeric composition of the fourth aspect of the present invention is preferably prepared by mixing, more preferably dissolving, a polycyclohexadiene homo or copolymer of general formula IV in a precursor or monomer for a suitable polymer and effecting polymerisation of the precursor or monomer under conditions such that at least a substantial proportion of, and preferably substantially all, the cyclohexenyl rings in the polycyclohexadiene homo or copolymer of general formula IV are aromatised. For example, the polycyclohexadiene homo or copolymer may be dissolved in polyethylene terephthalate "prepolymer" and the polyethylene terephthalate "prepolymer" may be polymerised, by known techniques, at temperatures in the range of for example, 240° C. to 300° C., to form a polymeric blend.

Alternatively, a first polymeric blend may be prepared from a polycyclohexadiene homo or copolymer of general formula IV and a suitable polymer, e.g. polystyrene or polyphenylene oxide, for example by melt or solution blending, and the first polymeric blend may be treated, e.g. heated, such that elimination of at least a substantial proportion of the 1,2-disubstituents in the polycyclohexadiene homo or copolymer of general formula IV is effected to give a second polymeric blend comprising a polymeric composition of the fourth aspect of the present invention and a suitable polymer. Where, in a polymeric blend comprising a polymeric composition of the fourth aspect of the present invention, the aforesaid polymeric composition is a polyphenylene the degree of aggregation of the polyphenylene polymer may be determined by neutron scattering in the solid state.

A sixth aspect of the present invention provides a monomer of general formula

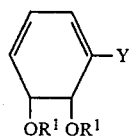

V wherein $R^1$ and Y have the meanings hereinbefore ascribed to them except that (a) where Y is H, $R^1$ is not $CH_3CO-$; (b) where Y is H, and the $OR^1$ groups are trans to each other, $R^1$ is not $C_6H_5CO-$; and (c) where Y is $CH_3$ and the $OR^1$ groups are cis to each other, $R^1$ is not $CH_3CO-$.

The various aspects of the present invention will now be described by reference to the following Examples which are illustrative of the invention.

PREPARATION OF CIS-1,2-DIHYDROXYCYCLOHEXA-3,5-DIENES

A mutant of *Pseudomonas putida* NC1B 11680 was prepared using N-methyl-N'-nitro-N-nitrosoguanidine as mutagen in the procedure of Ornston, Journal of Biological Chemistry, 1966, Volume 241, pages 3800-3810.

This mutant was used in the procedures described by Gibson, Hersley, Yoshioka and Mabry, Biochemistry, 1970, Volume 9, pages 1626-1630 and Gibson, Cardini, Maseles, and Kallio, Biochemistry, 1970, Volume 9, pages 1631-1635 with the appropriate aromatic compound.

PREPARATION OF TRANS-1,2-DIACETOXYCYCLOHEXA-3,5-DIENE trans-1,2-Diacetoxycyclohexa-3,5-diene was synthesised from 1,4-cyclohexadiene by the method of Platt et al (Synthesis, 1977 Volume 7, pages 449-50),

PREPARATION OF CIS-1,2-DIACETOXY-3-METHYL-CYCLOHEXA-3,5-DIENE cis-1,2-diacetoxy-3-methyl-cyclohexa-3,5-diene was prepared from cis-1,2-dihydroxy-3-methyl-cyclohexa-3,5-diene and acetyl chloride using the procedure as hereinafter described in Procedure A of Examples 1-5. It had a boiling point of 120° C. at 0.01 mm Hg.

PREPARATION OF CIS-1,2-DIACETOXY-CYCLOHEXA-3,5-DIENE cis-1,2-diacetoxy-cyclohexa-3,5-diene was prepared from cis-1,2-dihydroxy-cyclohexa-3,5-diene and acetic anhydride using the procedure as hereinafter described in Procedure B of Examples 1-5. It had a boiling point of 83°-84° C. at 0.07 mm Hg.

BENZOYL PEROXIDE

Benzoyl peroxide was dried at 20° C. and 0.01 mm mercury for 4 hours before use.

PREPARATION OF POLYETHYLENETEREPHTHALATE "PREPOLYMER"

A mixture of dimethylterephthalate (48.54 g, 0.25 moles), ethyleneglycol (34.16 g, 0.53 moles) and manganese diacetate tetrahydrate (18.4 mg, 7.5 μmol) was heated, with agitation, under distillation until approximately the theoretical amount (16 g, 0.25 mol) of methanol had been evolved. A solution (420 μl) of orthophosphoric acid (16.8 μl) in methanol (403 μl) was added by syringe to precipitate the catalyst as manganese phosphate and the residual traces of methanol were removed under reduced pressure. The mixture was allowed to cool to give a solid polyethylene terephthalate prepolymer.

EXAMPLES 1-5

General methods for the preparation of acyl and carbonate derivatives of cis-1,2-dihydroxycyclohexa-3,5-diene and homologues thereof

(a) Procedure A

An ice-chilled solution of the appropriate acyl halide or chloroformate (8 mmol) dissolved in dry toluene (4 ml) or, when not readily soluble in toluene, in dry diethylether (4 ml), was added dropwise to a stirred solution of the 1,2-dihydroxy-cyclohexa-3,5-diene (4 mmol) in dry pyridine (4 ml) at 0°-5° C. at such a rate that the temperature of the mixture did not rise above 8° C. After stirring at 0°-5° C. for 0.5 hours the cooling source was removed and the reaction mixture was stirred at 20° C. for a further 1 hour. Solvent was removed under reduced pressure (30°–40° C. bath), the residue was dissolved in chloroform or diethyl ether, washed successively with aqueous sodium carbonate and water, and dried (Na$_2$SO$_4$ or MgSO$_4$). Evaporation of the filtered solvent gave the crude acyl derivative which was purified by recrystallisation and/or distillation. Details of the purification and products are given in Table 1.

(b) Procedure B

Acetic anhydride (7.5 ml) was added dropwise to a stirred solution of the 1,2-dihydroxycyclohexa-3,5-diene (1.0 g) in pyridine (2.5 ml) at 0.5° C. at such a rate that the temperature of the mixture did not rise above 6° C. The cooling source was removed, the reaction mixture was stirred at 20° C. for a further 1 hour, and then worked-up as described in Procedure A to give a crude diacetate derivative which was purified by distillation and/or recrystallisation. Details of the purification and products are given in Table 1.

EXAMPLE 6

This example illustrates the preparation of poly(1,2-cis-diacetoxycyclohexa-3,5-diene) from neat monomer.

A mixture of freshly distilled cis-1,2-diacetoxycyclohexa-3,5-diene (2.5 g, 12.2 mmole) and benzoyl peroxide (8.5 mg, 35 μmole) in a glass tube was degassed under reduced pressure, frozen, and the glass tube was sealed. After 40 hours at 75° C. the tube was opened and the contents thereof, in the form of a clear glass-like polymer, were dissolved in chloroform. The chloroform solution was concentrated and the polymer was precipitated by the addition of methanol. The solid was filtered and dried at reduced pressure to give poly-(1,2-cis-diacetoxycyclohexa-3,5-diene) as a fluffy white solid (1.84 g, 77%). The infra-red spectrum of the polymer (as a KBr disc) had peaks at 2920 (C—H); 1740 (—COOH$_3$); 1370 (—OAc); and 1240 and 1040 (C—O) cm$^{-1}$. The proton magnetic resonance spectrum of the polymer in deuterochloroform at 29° C. gave signals at δ2.05 (6H, broad singlet, 2×CH$_3$CO—); δ2.60 (2H, very broad, >CHCH=CHCH<); δ60–6.1 (4H, very broad signal with peaks at δ5.2 and 5.6, 2×>C̲HOAc

TABLE 1 cis-1,2-Disubstituted-cyclohexa-3,5-dienes

| Example | Compound[f] | Procedure | Purification | Yield of Purified Product % | Melting Point °C. | Boiling Point °C. | Infra-Red Analysis (cm$^{-1}$) | Proton Magnetic Resonance Spectra (δ) |
|---|---|---|---|---|---|---|---|---|
| 1 | OCOPh OCOPh | A | Crystallisation from CHCl$_3$/pentane | 50 | 93 | | 1730, 1710, 1595, 1315, 1300 1265, 1240, 1115, 1100, 710[a] | 5.8 (2H, broad singlet) 5.9–6.4 (4H, multiplet) 7.2–7.6 (6H, multiplet) 7.6–7.9 (4H, multiplet)[c] |
| 2 | —CH$_3$ OCOPh OCOPh | A | Crystallisation from hexane | 46 | 82 | | 1715, 1595, 1370, 1310, 1290 1255, 1240, 1105, 1090, 1065, 1420, 705[a] | 1.95 (3H, singlet) 5.75–6.25 (5H, multiplet) 7.2–7.6 (6H, multiplet) 7.8–8.0 (4H, multiplet)[d] |
| 3 | [e] OCOCMe$_3$ OCOMe$_3$ | A | Distillation | 48 | | 83–86/ 0.05 mmHg | 1733, 1460, 1397, 1294 1278, 1160, 1143, 1053 980, 720,[b] | 1.20 (18H, singlet) 5.48 (2H, singlet) 5.7–6.2 (4H, multiplet)[d] |
| 4 | OCO$_2$Me OCO$_2$Me | A | Distillation | 48 | | 105/ 0.01 mmHg | 2960, 1751, 1445, 1300 1275, 1250, 1024, 971 788[b] | 3.79 (6H, singlet) 5.4 (2H, singlet) 5.83–6.24 (4H, multiplet)[d] |
| 5 | —Cl OAc OAc | B | Crystallisation from pentane | 57 | 42–44 | 140/0.1 mmHg | 1745, 1645, 1575, 1430, 1370 1265, 1235, 1215, 1170, 1115 1075, 1045, 1015, 980, 930 890, 785[b] | 2.05 (3H, singlet) 2.10 (3H, singlet) 5.5–5.9 (3H, multiplet) 5.9–6.15 (1H, multiplet) 6.25 (1H, doublet)[d] |

[a]In nujol.
[b]KBr disc.
[c]D6-dimethyl sulphoxide
[d]Deuterochloroform.
[e]Hereinafter referred to for convenience as "benzene-cis-glycol-dimethylcarbonate".
[f]cis-isomers.

and —CH=CH—). The $C^{13}$ magnetic resonance spectrum of the polymer in deuterochloroform at 29° C. gave signals at δ20.97 (CH$_3$CO—, sharp); δ39.84 (broad, >CHCH=CH—); δ68.96 (broad, >COAc); δ127.32 (broad, —CH=CH—); δ169.97 (sharp, —COCH$_3$). The weight average molecular weight (absolute) of the polymer determined by low angle laser light scattering in ethylene dichloride was 103600 (±2%) and in methyl ethyl ketone was 1.03×10$^5$. The glass transition temperature and the decomposition temperature of the polymer were 209° C. and 260° C. respectively and its radius of gyration (measured in methyl ethyl ketone) was 26 nanometers.

EXAMPLES 7-9

These examples illustrate the solution preparation of poly(1,2-cis-diacetoxycyclohexa-3,5-diene).

A mixture of cis-1,2-diacetoxycyclohexa-3,5-diene (500 mg, 2.6 mmol) and benzoylperoxide (9 mg, 37 μmol) in solvent (2.0 ml) in a glass tube was degassed under reduced pressure, frozen, and the tube was sealed. The contents were stirred (magnetic follower) for a specified time at 80° C. The tubes were opened and the contents were added to chloroform. The solution was concentrated and poly(1,2-cis-diacetoxycyclohexa-3,5-diene) was precipitated by the addition of hexane. The polymer was characterised by infra-red spectroscopy and gel permeation chromatography. Details of the preparation and products are given in Table 2.

EXAMPLES 10 and 11

These examples illustrate the suspension preparation of poly(1,2-cis-diacetoxycyclohexa-3,5-diene).

A mixture of cis-1,2-diacetoxycyclohexa-3,5-diene (500 mg, 2.6 mmol), benzoylperoxide (9 mg, 37 μmol) and organic liquid (2 ml) in a glass-tube was degassed under reduced pressure, frozen, and the tube was sealed. The contents were vigorously stirred to disperse the 1,2-diacetoxycyclohexa-3,5-diene in the organic liquid. After 17 hours at 80° C. the tube was opened and the contents were dissolved in chloroform. The chloroform solution was concentrated and the polymer was precipitated by the addition of hexane. The precipitate was filtered, washed with hexane, and dried under reduced pressure, to give poly(1,2-cis-diacetoxycyclohexa-3,5-diene).

TABLE 2

Solution Preparation of Poly (1,2-cis-diacetoxycyclohexa-3,5-diene)

| | Reaction conditions | | Product | |
|---|---|---|---|---|
| Example | Solvent | Time (hours) | Yield (%) | Mw$^{a,c}$ | Dispersity$^{b,c}$ |
| 7 | Benzene | 43 | 14 | 50,603 | 2.55 |
| 8 | Toluene | 72 | 80 | 53,200 | 4.61 |
| 9 | Methylene Chloride | 42 | 2 | 16,649 | 2.00 |

$^a$Weight average molecular weight.
$^b$Dispersity = $\frac{\text{weight average molecular weight}}{\text{number average molecular weight}}$
$^c$Determined by gel permeation chromatography.

In Example 10, the organic liquid was perfluoro-1-methyldecalin and the yield of polymer was 67%.

In Example 11, the organic liquid was tetrafluoroethylene tetramer and the yield of polymer was 41%.

EXAMPLE 12

This example illustrates the preparation of poly(1,2-cis-dibenzoyloxycyclohexa-3,5-diene).

A mixture of cis-1,2-dibenzoyloxycyclohexa-3,5-diene (600 mg, 1.88 mmole) and benzoyl peroxide (3 mg, 12.4 μmol) in a glass tube was degassed under reduced pressure, frozen and the tube was sealed. After 18 hours at 97°-98° C. the tube was opened and the contents, in the form of a clear glass-like polymer, were dissolved in chloroform. The chloroform solution was filtered, concentrated, and the polymer was precipitated by the slow addition of n-heptane (150 ml). The filtered precipitate was washed with pentane, and dried under reduced pressure to give poly(1,2-cis-dibenzoyloxycyclohexa-3,5-diene)(450 mg, 75%). The infrared spectrum of the polymer (as a film on NaCl) had peaks at 1720 (—COAr); 1600, 1580 (Ar); 1445, 1310, 1215 (broad, 1170, 1105, 1090, 1065, 1020 and 705 cm$^{-1}$. The proton magnetic resonance spectrum of the polymer in D-6 dimethyl sulphoxide at 29° C. gave signals at δ4.80–6.40 (believed to be —CH =CH— and 2×>CHOCOPh); and δ6.40–8.40 (believed to be aromatic hydrogens). The weight average molecular weight (absolute) of the polymer determined by low angle laser light scattering in ethylene dichloride was 206,000.

EXAMPLE 13

This example illustrates the preparation of poly(1,2-cis-dibenzoyloxy-3-methylcyclohexa-3,5-diene).

A mixture of cis-1,2-dibenzoyloxy-3-methylcyclohexa-3,5-diene (1.50 g, 4.5 mmol) and benzoylperoxide (12 mg, 49.6 μmol) in a glass tube was degassed under reduced pressure, frozen and the tube sealed. After 17 hours at 90°-95° C. the tube was opened, the contents were dissolved in chloroform and the polymer was precipitated by the addition of methanol. The precipitate was filtered and dried under reduced pressure to give poly(1,2-cis-dibenzoyloxy-3-methylcyclohexa-3,5-diene) (66 mg, 0.04%). The infra-red spectrum of the polymer (as a KBr disc) had peaks at 1730(—CO); 1600, 1580 (Ar); 1445; 1110, 1270, 1175, 1105, 1095, 1065, 1020, and 705 cm$^{-1}$. The proton magnetic resonance spectrum of the polymer in deuterochloroform at 40° C. gave signals at δ0.40–2.0 (3H, very broad resonance with peaks at δ1.25 and 1.70, CH$_3$—C≡); δ2.20–3.80 (about 1.5H, very broad signal); δ4.80–8.20 [(very broad signal with peaks at δ5.90 (integrating about 4H and believed to correspond to 2×>CHOCOPh and —CH=CH—) and δ7.20 and 7.70 (integrating for about 10H and believed to correspond to meta/para- and ortho- protons respectively of —COPh groups)].

EXAMPLE 14

This example illustrates the preparation of poly(3-chloro-1,2-cis-diacetoxycyclohexa-3,5-diene).

A mixture of 3-chloro-1,2-cis-diacetoxycyclohexa-3,5-diene (400 mg, 1.73 mmol) and t-butyl perbenzoate (4 mg, 20.6 μmol) in a glass tube was degassed under reduced pressure and the tube was sealed. After 72 hours at 96° C. the tube was opened and the contents were washed with methanol/pentane. The insoluble material was filtered off and dried to give poly(3-chloro-1,2-cis-diacetoxycyclohexa-3,5-diene)(18 mg, 0.05%). The infra-red spectrum of the polymer (as a KBr disc) had peaks at 1750 (—COCH$_3$); 1370 (—OAc); 1235 and 1045 (C—O) cm$^{-1}$. The proton magnetic resonance spectrum of the polymer in deuterochloroform at 29° C. gave signals at δ2.10 (3H, singlet, —COCH$_3$); δ2.15 (3H, singlet, —COCH$_3$); δ2.50–2.32

(1H, very broad >C$\underline{H}$CH=C<); and δ4.90-6.30 (4H, very broad, 2×>C$\underline{H}$OAc and —C$\underline{H}$=C$\underline{H}$—).

EXAMPLE 15

This example illustrates the preparation of poly(1,2-cis-dihydroxycyclohexa-3,5-diene).

A solution (200 ml) of sodium methoxide (prepared by dissolving 5 grams of sodium in 200 ml dry methanol) was added over 15 minutes to a solution of poly(1,2-cis-diacetoxycyclohexa-3,5-diene)(300 mg), prepared in Example 6 in hot methanol (250 ml). After the addition of about 50 ml the solution became cloudy and a fluffy white precipitate was deposited. The mixture was gently refluxed for 20 hours then cooled and water (5 ml) was added. The precipitate was removed by filtration, washed successively with methanol and ice cold water and dried under reduced pressure to give poly(1,2-cis-dihydroxycyclohexa-3,5-diene) (145 mg, 85%). The infra-red spectrum of the product (KBr disc) had peaks at 2910 (C—H); 1400 and 1055 (C—O) cm$^{-1}$. The proton magnetic resonance spectrum of the product in D-6 dimethyl sulphoxide at 70° C. gave signals at δ3.40-4.60 (with maxima at δ3.65, 3.80 and 4.1) and δ5.20-6.0 (peaking at 5.50 with a shoulder at 5.65); integral intensities of the two broad signals were in the ratio of 2:1. The polymer product was found to be insoluble in acetone, chloroform, pyridine, nitrobenzene and dimethylformamide, slightly soluble in hot water, moderately soluble in dimethyl sulphoxide and readily soluble in trifluoroacetic acid.

EXAMPLES 16-28

These examples illustrate the preparation of a range of copolymers of cis-1,2-diacetoxycyclohexa-3,5-diene and styrene.

A mixture of cis-1,2-diacetoxycyclohexa-3,5-diene, benzoyl peroxide, and freshly distilled styrene in a glass tube was degassed, frozen, and the tube was sealed. After 40 hours at 80° C., the tube was opened and the polymeric product was recovered as in Example 6 to give copolymer of cis-1,2-diacetoxycyclohexa-3,5-diene and styrene. The infra-red spectrum of the polymers (as KBr discs) had peaks at 3030, 2930 (C—H); 1740 (CH$_3$CO—); 1600, 1495, 1455 (polystyrene); 1370 (—OAc/PS); 1245, 1225 (shoulder) (C—O); 1040, 1030 (C—O); 760 and 700 (Ar) cm$^{-1}$. The proton magnetic resonance spectrum of the copolymers in deuterochloroform at 29° C. gave signals at δ1.0-2.80 (broad signal with maxima at δ1.90, 2.05 and 2.30, Ar—CH—CH$_2$— in polystyrene and 2×CH$_3$CO— and >C$\underline{H}$C$\underline{H}$=CHCH<); δ4.20-5.80 (2×>CHOAc, —C$\underline{H}$=CH—); δ6.20-7.40 (maxima at δ6.65 corresponding to two orthoprotons, and 7.10 corresponding to one para- and two meta-protons); integral intensities gave the ratio of cyclohexenylene rings to styrene residues in the copolymer. The results are given in Table 3.

TABLE 3

| Example | Mole % cis-1,2-diacetoxy-3,5-cyclohexadiene in copolymer product | Glass Transition Temperature °C. |
|---|---|---|
| 16 | 2.5 | 110 |
| 17 | 11 | 127 |
| 18 | 22 | 135 |
| 19 | 39 | 138 |
| 20 | 53 | 157 |
| 21 | 70 | 167 |
| 22 | 81 | 175 |

TABLE 3-continued

| Example | Mole % cis-1,2-diacetoxy-3,5-cyclohexadiene in copolymer product | Glass Transition Temperature °C. |
|---|---|---|
| 23 | 89 | 182 |
| 24 | 91 | 190 |
| 25 | 92.5 | 202 |
| 26 | 93.5 | 202 |
| 27 | 95 | 202 |
| 28 | 97.5 | 208 |

EXAMPLE 29

This example illustrates the preparation of a copolymer of 3-chloro-cis-1,2-diacetoxycyclohexa-3,5-diene and styrene.

A mixture of 3-chloro-cis-1,2-diacetoxycyclohexa-3,5-diene (500 mg, 2.16 mmol), azobisisobutyronitrile (4 mg, 24.4 μmol) and freshly distilled styrene (180 mg, 1.73 mmol) in a glass tube was degassed, frozen, and the tube was sealed. After 36 hours at 60° C. the tube was opened and the contents were poured into methanol. The resulting precipitate was filtered, washed with methanol and dried under reduced pressure to give a copolymer (100 mgs) of 3-chloro-1,2-cis-diacetoxycyclohexa-3,5-diene and styrene. The infrared spectrum of the polymer (as a KBr disc) had peaks at 3030, 2930 (C—H); 1750 (—COCH$_3$); 1600; 1495, 1455 (polystyrene); 1370 (—OAc/PS); 1240, 1045 (C—O); and 700 (Ar) cm$^{-1}$. The proton magnetic resonance spectrum of the copolymer in deuterochloroform at 40° C. gave signals at δ1.20-2.60 (broad signal with maxima at δ1.52 and 2.10

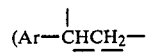

in polystyrene and 2×CH$_3$CO— and >C$\underline{H}$CH=CH—); δ4.4-5.8 (very broad signal, —C$\underline{H}$=CH— and 2×>CHOAc); δ6.3-7.4 (maxima at δ6.7 corresponding to two ortho protons, and δ7.1 corresponding to one para- and two meta-protons in polystyrene). Integral intensities indicated that the molar ratio of cyclohexenylene rings to styrene residues in the copolymer was 1:4.

EXAMPLE 30

This example illustrates the preparation of a copolymer of cis-1,2-diacetoxy-3-methylcyclohexa-3,5-diene and styrene.

A mixture of cis-1,2-diacetoxy-3-methylcyclohexa-3,5-diene (500 mg, 2.38 mmol), benzoyl peroxide (1.5 mg, 6.2 μmol), and freshly distilled styrene (400 mg, 3.85 mmol) in a glass tube was degassed, frozen, and the tube was sealed. After 40 hours at 90° C. the contents of the tube were isolated as in Example 6 to give a copolymer (110 mgs) of cis-1,2-diacetoxy-3-methylcyclohexa-3,5-diene and styrene. The infra-red spectrum of the copolymer (as a KBr disc) had peaks at 3030, 2930 (C—H); 1740 (—COCH$_3$); 1600, 1495, 1455 (polystyrene); 1370 (—OAc/PS); 1245, 1225 (shoulder) (C—O); 760 and 700 (Ar) cm$^{-1}$. The proton magnetic resonance spectrum of the copolymer in deuterochloroform at 29° C. and at 50° C. gave signals at δ1.0-2.40 (broad signal with maxima at δ1.55 and 1.90, ArCHCH$_2$— in polystyrene and 2×CH$_3$CO—, CH$_3$—C≡, and —CH=CH—CH< in diacetate δ4.30-5.50 (very broad signal, —CH=CH— and 2×>CHOAc); δ6.20–7.4 (maxima at δ6.6, corresponding to two ortho-protons, and δ7.05 corresponding to two meta- and one para-protons in polystyrene). Integral intensities indicated that the molar ratio of cyclohexenylene rings to styrene residues in the copolymer was about 1.5. The glass transition temperature of the copolymer (determined by DSC) was 113° C.

EXAMPLE 31

This example illustrates the preparation of a copolymer of cis-1,2-diacetoxy-3-methylcyclohexa-3,5-diene and methyl methacrylate.

A mixture of cis-1,2-diacetoxy-3-methylcyclohexa-3,5-diene (480 mg, 2.29 mmol), benzoylperoxide (1.5 mg, 6.2 μmol) and freshly distilled methyl methacrylate (470 mg, 4.7 mmol) in a glass tube was degassed, frozen, and the tube was sealed. After 40 hours at 90° C. the tube was opened and the contents thereof were recovered as in Example 6 to give a copolymer (240 mgs) of cis-1,2-diacetoxy-3-methylcyclohexa-3,5-diene and methyl methacrylate. The infra-red spectrum of the copolymer (as a KBr disc) had peaks at 3000, 2955 (C—H); 1740–1725 (—COCH$_3$ and —CO$_2$CH$_3$), 1485, 1450, 1435, 1270 (shoulder), 1245, 1195 and 1150 cm$^{-1}$. The proton magnetic resonance spectrum of the copolymer in deuterchloroform at 29° C. gave signals at δ0.50–1.40 (maxima at 0.90 and 1.05,

—CH$_2$C(CH$_3$)CO$_2$Me);

δ1.40–2.30 (maxima at 1.85 and 2.10,

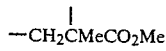

—CH$_2$CMeCO$_2$Me of PMMA and CH$_3$C≡, >CH—CH=CH— and 2×CH$_3$ CO— of acetate); 3.65 (—CO$_2$Me); 4.8–5.7 (—CH=CH— and 2×CHOAc). Integral intensities indicated that the molar ratio of cyclohexenylene rings to methacrylate residues in the copolymer was about 1:13. The glass transition temperature of the copolymer was 114° C.

EXAMPLE 32

This example illustrates the preparation of a polymer of benzene-cis-glycoldimethylcarbonate by dispersion polymerisation.

Benzene-cis-glycoldimethylcarbonate (12 g, 52.63 mmol) was placed in a 250 ml flask equipped with a paddle stirrer and degassed. The flask was filled with nitrogen azobisisobutyronitrile (84 mgs, 0.51 mmol), cyclohexane (84 mls) and dispersing agent (84 mgs, graft copolymer-backbone of polymethylmethacrylate, branches of poly-12-hydroxystearic acid) were added and the mixture homogenised at room temperature. The mixture was then heated in a bath held at 60° for 93 hours. The milky product (10.5 g, 87.5% yield) consisted of a dispersion of spherical particles (average size, 0.12 microns) in cyclohexane. The polymer was isolated by dissolving in methylene chloride followed by precipitation in hexane, isolation and vacuum drying.

Various molecular weight data was obtained. The I.V. in dichloroethane was 0.33 and low angle laser light scattering in the same solvent gave an $\overline{M}w$ value of 453811. G.P.C. molecular weights were measured as $\overline{M}n=32074$, $\overline{M}w=2320840$.

EXAMPLE 33

This example illustrates the polymerisation of benzene-cis-glycoldimethylcarbonate by the action of U.V. radiation.

Benzene-cis-glycoldimethylcarbonate (1 gram; 4.4 mmol) was degassed and sealed in a quartz glass tube. The tube was then held at a distance from a Phillips MLV 300W Ultra Violet Lamp so that its temperature was held at 40°. After 92 hours the tube was opened, the solid product was dissolved in methylene chloride and precipitated in hexane. The isolated and vacuum dried polymer (0.5 g, 50% yield) had an I.V. in 1,2-dichloroethane of 0.41, and G.P.C. molecular weights $\overline{M}n=88898$, $\overline{M}w=321849$.

EXAMPLE 34

This example illustrates the polymerisation of cis-1,2-dipivaloxycyclohexa-3,5-diene by a radical initiator in the bulk phase.

cis-1,2-Dipivaloxycyclohexa-3,5-diene (1 g, 3.57 mmol) was degassed in a glass tube containing benzoyl peroxide (6.3 mg, 0.026 mmol) and sealed under vacuum. After 24 hours at 80° the tube was opened and the solid contents dissolved in methylene chloride. The polymer was precipitated in methanol, isolated and vacuum dried. The polymer (0.8 g, 80% yield) had G.P.C. molecular weights $\overline{M}n=29940$, $\overline{M}w=77373$. The Tg of the polymer was 240° C.

EXAMPLE 35

This example illustrates the thermal polymerisation of cis-1,2-diacetoxycyclohexa-3,5-diene in the bulk phase.

cis-1,2-Diacetoxycyclohexa-3,5-diene (1 gram; 5.1 mmol) was degassed and sealed under vacuum in a glass tube. After 72 hours at 90° C., the tube was opened, the product was dissolved in methylene chloride and precipitated in hexane. The isolated and vacuum dried polymer (0.114 g, 11.4% yield) had G.P.C. molecular weight values of $\overline{M}n=54930$, $\overline{M}w=145510$. Low angle laser light scattering in 1,2-dichloroethane gave an $\overline{M}w$ value of 112500.

EXAMPLE 36

This example illustrates the copolymerisation of cis-1,2-diacetoxycyclohexa-3,5-diene with vinyl chloride.

cis-1,2-Diacetoxycyclohexa-3,5-diene (2.53 grams; 12.9 mmol) was degassed in a glass tube containing benzoyl peroxide (6 mg, 0.025 mmol). Vinyl chloride (10 mls, 108 mmol) was then distilled into the tube which was sealed off under vacuum. After 42 hours at 90° C. the tube was opened and the contents were poured into hexane. The isolated and vacuum dried copolymer (0.151 grams; 1.58% yield) was shown by microanalysis to contain 45 mol% vinyl chloride residues. The copolymer had a Tg of 144° C. The G.P.C. molecular weights of the copolymer were $\overline{M}n=2945$, $\overline{M}w=8369$.

EXAMPLE 37

This example illustrates the copolymerisation of cis-1,2-diacetoxycyclohexa-3,5-diene with chlorotrifluoroethylene.

cis-1,2-Diacetoxycyclohexa-3,5-diene (1 gram; 5.1 mmol) was degassed in a glass tube containing benzoyl peroxide (4 mgs, 0.017 mmol) and chlorotrifluoroethylene (1 ml, 8.6 mmol) was distilled in and sealed off under vacuum. After 20 hours at 90° C. the tube was opened, the solid contents dissolved in methylene chloride and precipitated in hexane. The isolated and vacuum dried copolymer (0.15 grams, 15% yield) was estimated by microanalysis to have 10 mole % chlorotrifluoroethylene residues incorporated in its structure. The Tg of the copolymer was 182° C. The G.P.C. molecular weights of the copolymer were $\overline{M}n=22969$, $\overline{M}w=56443$.

EXAMPLE 38

This example illustrates the copolymerisation of benzene-cis-glycoldimethylcarbonate with 1,3-butadiene-$d^6$.

Benzene-cis-glycoldimethylcarbonate (2 g, 8.8 mmol) was degassed in a tube containing azo-bis-isobutyronitrile (10 mg, 0.061 mmol) and 1,3-butadiene-$d^6$ (1.7 ml, 19.8 mmol) was distilled in and sealed off under vacuum. After 60 hours at 50° the tube was opened, the solid contents dissolved in methylene chloride and precipitated in hexane. The isolated and vacuum dried polymer (1.3 grams, 40.8% yield) had a Tg of $-15°$ C. The G.P.C. molecular weight values were $\overline{M}n=50155$ and $\overline{M}w=148997$. The proton magnetic resonance spectrum of the polymer in deuterochloroform at 29° C. gave signals at $\delta 2.6$ (2H, doublet, >CH—CH=-CH—)-$\delta 3.8$ (6H, sharp singlet, CH$_3$O—), $\overline{\delta}4.93$ (2H, doublet, >C$\underline{H}$O) and $\delta 5.6$ (2H, singlet, —CH=CH—)

EXAMPLE 39

This example illustrates the preparation of poly-trans-1,2-diacetoxycyclohexa-3,5-diene) from neat monomer.

A mixture of freshly distilled trans-1,2-diacetoxycyclohexa-3,5-diene and benzoyl peroxide in a monomer/catalyst ratio of 102/1 in a glass tube was degassed under reduced pressure, frozen, and the glass tube was sealed. After 43 hours at 90° C. the tube was opened and the contents thereof, in the form of a clear glass-like polymer, were dissolved in chloroform. The chloroform solution was concentrated and the polymer was precipitated into hexane. The solid was filtered and dried at reduced pressure to give poly(1,2-trans-diacetoxycyclohexa-3,5-diene) as a fluffy white solid (49% conversion), $M_w=10240$ and $M_n=5770$.

EXAMPLES 40–42

Preparation of polymeric blends comprising Poly(1,2-disubstitutedcyclohexa-3,5-dienes)

Procedure A

The matrix polymer and the poly(1,2-disubstituted-cyclohexa-3,5-diene) were each dissolved in a common solvent and the two solutions were blended together. The solvent is removed under reduced pressure to give the crude blend of polymers.

Procedure B

The matrix polymer and the 1,2-disubstituted-cyclohexa-3,5-diene are each dissolved in a common solvent and the two solutions are blended together. A solid blend of the two polymers is then produced by their precipitation in a common non-solvent. The solid is filtered, washed and dried under reduced pressure.

The results are shown in Table 4.

The presence of poly(benzene-cis-glycoldimethylcarbonate) in the blends of Examples 40 and 41 was readily detected by infra-red spectroscopy.

TABLE 4

Polymeric Blends comprising Benzene-cis-glycol-dimethylcarbonate

| Example | Matrix Polymer (Weight in grams) | Weight of Benzene-cis-glycol-dimethylcarbonate (grams) | Common Solvent | Procedure |
|---------|----------------------------------|-------------------------------------------------------|----------------|-----------|
| 40 | Polystyrene (0.5) | 0.2 | CHCl$_3$ | A |
| 41 | Poly-2,6-dimethyl-phenylene oxide (0.5) | 0.2 | CHCl$_3$ | A |
| 42 | Polyethylene terephthalate (10.0) | 1.0 | CF$_3$CO$_2$H | B |

EXAMPLE 43

This example illustrates the preparation of polyparaphenylene.

A colourless film of poly-3,6(1,2-cis-diacetoxycyclohexa-3,5-diene) was dissolved onto a microscope slide from a solution of the polymer (50 mg) in dichloromethane (1 ml). The temperature of the film was raised, in a substantially oxygen-free atmosphere, over 2 hours to 320° C. and was held at this temperature for 3 hours to give a pale yellow film.

The infra-red spectrum of the pale yellow film (as KBr disc) had no peaks which corresponded to CH$_3$—CO—, it has peaks at 1480, 1000 and 810 cm$^{-1}$, and it was very similar to a published spectrum of poly(-paraphenylene) (M. B. Jones, P. Kovacic and D. Lanska, Journal of Polymer Science, Polymer Chemistry, 1981, Volume 19, pages 89–107).

EXAMPLES 44–49

These examples illustrate the preparation of aromatic polymers according to the present invention.

GENERAL METHOD A

Evaporation of an approximately 20% w/w solution of poly-(cis-1,2-disubstituted-cyclohexa-3,5-diene) in chloroform, which solution optionally contained an antioxidant, Irganox 1010 (about 1% w/w of polymer), and/or an elimination catalyst, e.g. potassium bromide (about 1 mole %), under reduced pressure afforded a film of the polymer.

The film was heated to a specified temperature for a specified length of time. The rate of aromatisation was determined in independant experiments by isothermal gravimetric analysis (TGA) and by infra-red analysis.

The product was analysed by infra-red spectroscopy, TGA, solid state proton magnetic resonance spectroscopy and X-ray crystallography and the analyses were found to be substantially consistent with the reported data for poly-p-phenylene. (J. G. Speight, P. Kovacic and F. W. Koch, Journal of Macromolecular Science, Reviews of Macromolecular Chemistry, 1971, Volume C5, pages 295–386).

METHOD B (EXAMPLE 49)

Poly(cis-1,2-disubstituted-cyclohexa-3,5-diene) powder, optionally containing an antioxidant or elimination catalyst was treated to a specified thermal cycle. Analysis of the product as described in Method A confirmed that it was substantially poly-p-phenylene.

The results are given in Table 5.

EXAMPLE 50

This example illustrates the use of a base to catalyse elimination of 1,2-substituents from poly(cis-1,2-disubstituted-cyclohexa-3,5-diene) in the third aspect of the present invention.

TABLE 5

| | Starting Material | | Additives | | Reaction Conditions | | Rates of Aromatisation | | Weight of Product (grams) |
|---|---|---|---|---|---|---|---|---|---|
| Example | Source (Example No.) | Weight (grams) | Antioxidant[a] (mgs) | Catalyst[b] (mgs) | Temperature (°C.) | Time (hours) | Approximate Half-life (minutes) | Temperature (°C.) | |
| 44 | 6 | 1.7 | — | — | 300 | 8 | 14 | 300 | 0.50 |
| 45 | 34 | 5.0 | 50 | — | 300 | 4 | 18 | 300 | 1.14 |
| 46 | 12 | 5.0 | 50 | — | 300 | 4 | 20 | 300 | 0.95 |
| 47 | 32 | 3.0 | — | — | 300 | 4 | 11 | 280 | 0.90 |
| 48 | 32 | 1.0 | — | 31 | 300 | 2.3 | — | — | 0.30 |
| 49 | 32 | 0.2 | — | — | 270 | 8 | — | — | — |

[a] = Irganox 1010
[b] = KBr

A solution of sodium methoxide, prepared by dissolving sodium (4.6 grams) in methanol (50 ml), was added dropwise over 5 minutes to a refluxing solution of poly-benzene-cis-glycoldimethylcarbonate (2.28 grams) in tetrahydrofuran (200 ml). The mixture was cooled, filtered, and the filtered product was washed sequentially with water, methanol and pentane. Analysis of the dried product (0.7 grams) by infra-red spectroscopy, showed the product to be substantially poly-p-phenylene.

EXAMPLE 51

This example illustrates production of an aromatic polymer according to the present invention.

A solution of poly-benzene-cis-glycoldipivalate (5 grams) in squalane (100 ml) was refluxed under nitrogen for 8.5 hours. An increasing quantity of a pale yellow precipitate was produced over the duration of the experiment. The mixture was cooled, filtered and washed with pentane. Analysis of the product was consistent with the formation of poly-phenylene. The infra-red spectrum, showed about 90% aromatisation while X-ray analysis (ratio of crystalline reflections to amorphous halos) suggested about 40% crystallinity.

EXAMPLES 52-54

These examples illustrate production of aromatic polymers according to the present invention in fibre form.

A solution of poly(cis-1,2-disubstituted-cyclohexa-3,5-diene) in a suitable solvent, optionally containing an anti-oxidant, e.g. Irganox 1010 (0.1% by weight of polymer) was dry spun and the solvent flashed off to give a fibre the diameter of which may be varied by altering relevant conditions, e.g. wind-up rate.

TABLE 6

| Example | Starting Material | Intrinsic Viscosity (deciliters/gram in 1,2-dichloroethane at 30° C.) | Spinning Solution | | Diameter of Fibre (microns) | Aromatisation Conditions | | Product % Aromatic |
|---|---|---|---|---|---|---|---|---|
| | | | Solvent | Concentration (w/w) | | Temperature (°C.) | Time (Hours) | |
| 52 | A | 0.30 | CH$_2$Cl$_2$ | 50 | 170 | 200 | 16 | |
| | | | | | | 300 | 35 | |
| 53 | B | 0.15 | CH$_2$Cl$_2$ | 55 | 230 | 245 | 16 | 90 |
| | | | | | | 300 | 18 | |
| 54 | C | 0.50 | CH$_2$Cl$_2$ | 40 | 200 | 185 | 16 | 95 |
| | | | | | | | 300 | 3 | |

A: poly (1,2-cis-diacetoxycyclohexa-3,5-diene)
B: poly (1,2-cis-dipivaloxycyclohexa-3,5-diene)
C: poly (benzene-cis-glycoldimethylcarbonate)

The aformentioned fibre is held under tension in an oxygen-free atmosphere and the temperature thereof is raised to a specified value for a specified time.

The results are given in Table 6.

EXAMPLE 55-56

These examples illustrate the aromatisation of a range of cis-1,2-diacetoxycyclohexa-3,5-diene/styrene copolymers.

A series of cis-1,2-diacetoxycyclohexa-3,5-diene/styrene copolymers (2.5–97.5 mole % styrene) were aromatised as described in Method A of Examples 44–49. Aromatised products which contained up to 70 mole % aromatic residues were completely soluble in methylene chloride.

The glass softening points of the polymers containing from 25 to 93 mole % phenylene residues are shown in Table 7.

TABLE 7

| Example | Source of Starting Material (Example No) | Mole % p-phenylene in copolymer | Softening Point (°C.) |
|---|---|---|---|
| 55 | 18 | 25 | 95 |
| 56 | 19 | 39 | 99 |
| 57 | 20 | 53 | 107 |
| 58 | 21 | 70 | 130 |
| 59 | 22 | 81 | 154 |
| 60 | 23 | 89 | 179 |
| 61 | 24 | 90 | 254 |
| 62 | 25 | 93 | 233 |

EXAMPLE 63

This example illustrates the aromatisation of poly(1,2-trans-diacetoxycylohexa-3,5-diene).

A thin film of poly(1,2-trans-diacetoxycyclohexa-3,5-diene), prepared in Example 39, was solution cast (from chloroform) on to a potassium bromide disc. The disc was then placed in a nitrogen purged oven contained within an infra-red spectrophotometer such that the optical path passed through the windown and film. The disc was then heated to 285° C. Regular monitoring of the spectrum demonstrated the loss of acetate groups and the appearance of pholyphenylene.

EXAMPLES 64-66

These examples illustrate the preparation of polymeric blends comprising aromatic polymers according to present invention.

Polymeric blends prepared in Examples 40-42 were heated at elevated temperature in an oxygen-free atmosphere.

The presence of poly-phenylene in the resulting blend was shown by infra-red spectroscopy and/or by dissolution of the matrix polymer in an appropriate solvent to leave an insoluble residue of polyphenylene.

The results are given in Table 8.

TABLE 8

| Example | Starting blend (Obtained in Example) | Weight of Blend (gram) | Weight of Residual Polyphenylene (grams) | Aromatisation Conditions | | |
|---|---|---|---|---|---|---|
| | | | | Temperature °C. | Time (hrs) | Dissolution Solvent |
| 64 | 40 | 0.5 | 0.06 | 260 | 5.5 | CHCl$_3$ |
| 65 | 41 | 0.5 | 0.06 | 260 | 5.5 | CHCl$_3$ |
| 66 | 42 | 10.0 | a | 285 | 4.5 | Sodium glycolate | a = Not determined

We claim:

1. A polymeric composition comprising a polymer which has a structure which may be represented by general formula:

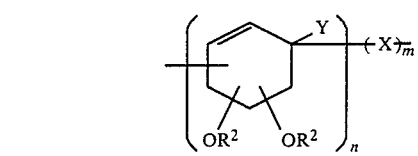

wherein the cyclohexenylene ring and the residue X, where X is present, may vary from unit to unit along the polymer chain; each $R^2$, which may be the same or different, is hydrogen, acyl or hydrocarbyloxyketo; X, where present, is the residue of a polymerisable vinyl comonomer, the $OR^2$ groups are on adjacent carbon atoms, Y is hydrogen, halogen or an alkyl group having up to four carbon atoms; n and m are whole numbers; and the ratio of n:m lies in the range 1:0 to 1:1000.

2. A polymeric composition as claimed in claim 1 wherein the $OR^2$ groups are cis to each other.

3. A polymeric composition as claimed in claim 1 wherein X is

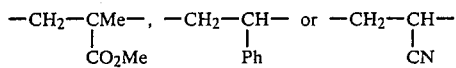

4. A polymeric composition as claimed in claim 1 wherein Y is hydrogen.

5. A polymeric composition as claimed in claim 1 wherein m is 0.